United States Patent
Lasner et al.

(10) Patent No.: US 10,499,943 B2
(45) Date of Patent: Dec. 10, 2019

(54) RING HANDLED SURGICAL INSTRUMENT

(71) Applicants: Michael E Lasner, Mt Kisco, NY (US); Jeffrey I Lasner, Purchase, NY (US)

(72) Inventors: Michael E Lasner, Mt Kisco, NY (US); Jeffrey I Lasner, Purchase, NY (US)

(*) Notice: Subject to any disclaimer, the term of this patent is extended or adjusted under 35 U.S.C. 154(b) by 0 days.

(21) Appl. No.: 15/867,682

(22) Filed: Jan. 10, 2018

(65) Prior Publication Data

US 2018/0193051 A1    Jul. 12, 2018

Related U.S. Application Data

(60) Provisional application No. 62/498,977, filed on Jan. 11, 2017.

(51) Int. Cl.
*A61B 17/3201* (2006.01)
*A61B 17/28* (2006.01)

(52) U.S. Cl.
CPC ...... *A61B 17/3201* (2013.01); *A61B 17/2841* (2013.01)

(58) Field of Classification Search
CPC .................. A61B 17/3201; A61B 17/2841
USPC .......................................................... 30/254
See application file for complete search history.

(56) References Cited

U.S. PATENT DOCUMENTS

| | | | | |
|---|---|---|---|---|
| 3,003,236 | A * | 10/1961 | Castelli | A61B 17/0467 30/234 |
| 4,038,750 | A * | 8/1977 | Moran, Jr. | B26B 13/12 30/254 |
| 4,527,331 | A * | 7/1985 | Lasner | A61B 17/3201 30/135 |
| 6,592,603 | B2 * | 7/2003 | Lasner | A61B 17/2841 30/261 |
| 2004/0098007 | A1 * | 5/2004 | Heiss | A61B 17/320016 606/174 |
| 2006/0009795 | A1 * | 1/2006 | Lasner | A61B 17/30 606/174 |
| 2010/0005929 | A1 * | 1/2010 | Ahlberg | A61B 17/320016 76/106.5 |
| 2014/0182424 | A1 * | 7/2014 | Lasner | A61B 17/2812 81/427.5 |
| 2014/0309676 | A1 * | 10/2014 | Slater | A61B 17/320016 606/170 |
| 2018/0193051 | A1 * | 7/2018 | Lasner | A61B 17/3201 |
| 2018/0206872 | A1 * | 7/2018 | Matsuo | A61B 17/3201 |

\* cited by examiner

*Primary Examiner* — Hwei-Siu C Payer
(74) *Attorney, Agent, or Firm* — Joseph M. Fowler

(57) ABSTRACT

A ring handled surgical instrument is disclosed which can act as a scissors, a blunt dissector and a gripper. The device is made from flexibly resilient, medical grade sheet material in which the handles are strong enough to withstand without flexion the closure forces imparted by the fingers of a clinician and yet allow the blades on the operative end of the scissors to remain flexibly springy.

2 Claims, 7 Drawing Sheets

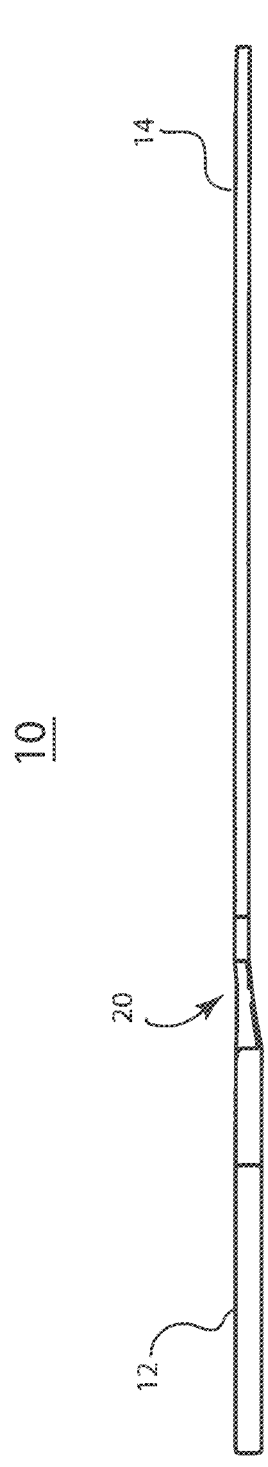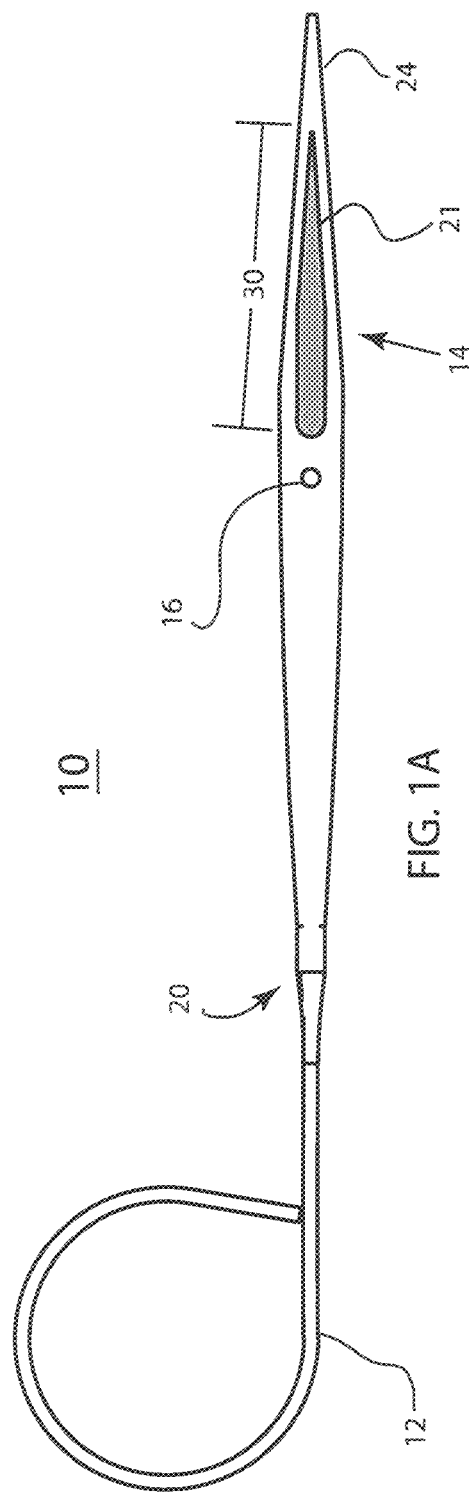

RING HANDLED SURGICAL INSTRUMENT

CROSS-REFERENCE TO RELATED APPLICATIONS

The present application claims the benefit of U.S. Provisional Patent Application No. 62/498,977, filed on Jan. 11, 2017, which is expressly incorporated herein in its entirety by reference thereto.

In addition, U.S. Pat. Nos. 4,527,331; 6,592,603; and 7,497,867 are expressly incorporated herein in their entireties by reference thereto.

FIELD OF THE INVENTION

The present invention relates to ring handled surgical instruments that can be used in all aspects of surgery as scissors, forceps, needle holders and other devices.

BACKGROUND OF THE INVENTION

The use of sheet metal handles made from flexibly resilient, medical grade material has been pioneered by the present inventors beginning notably with U.S. Pat. No. 4,527,331 which addressed the problem of how to create a low cost, high quality scissors that opened automatically after closure. This development was followed by U.S. Pat. No. 6,592,603 which incorporated interlocking springs joining the ends of each pair of handles which significantly reduced the pressure needed to close the paired handles. Additional improvements in sheet metal and forceps were taught in U.S. Pat. No. 7,497,867. The present invention relates specifically to ring handled devices and incorporates flexibly resilient sheet metal stampings and/or laser cut components in place of more conventional forged, cast or machined components. Earlier attempts to make precision grade surgical scissors from flexible sheet metal components have suffered from specific limitations inherent in adapting sheet metal strips to the entire scissors construction.

BRIEF SUMMARY OF THE INVENTION

A primary object of the present invention is to provide a pair of surgical scissors with ring handles constructed entirely from sheet metal material strong enough to withstand without flexion the closure forces imparted by the fingers of a surgical clinician and yet allow the jaw blades on the working or operative end of the scissors to remain flexibly springy. The flexibly springy bladed jaws provide adequate shearing bias for effective cutting while also servings—simultaneously or sequentially—as the primary tool for smoothly controllable blunt dissection. Another object of the invention is to act as a gripper when required in an appropriate surgical circumstance. In order to accomplish the foregoing objectives, the working end of the scissors has been made more resiliently flexible by reducing substantially the mass of material near the cutting edge of the surgical instrument thereby enabling the operative ends of the instrument, when the handles are separated and scissors is opened, to flex to a greater degree orthogonally with respect to the pivotal plane of action of the scissors.

The scissors surgical instrument is comprised of a "pair" of scissors, literally, a pair of component halves constructed using one strip of sheet metal material pivotally connected together. Each component half has a handle end and a working or operative end. The handle end extends in the opposite longitudinal direction from the operative end. An accommodation for a pivot mechanism is located on each sheet metal component at some point between the handle and working ends. The operative working end of each half of the scissors has a blade and/or gripping structure. The handle end of each component half of the scissors may be formed into a shape adapted to fit a clinician's fingers. In addition, the handle end may be formed at the end of a 90 degree twist of a portion of the sheet metal strip between the handle end and the operative end of the scissors component.

The sheet metal blank forming a component half of the scissors may be formed by metal stamping, laser cutting or by other appropriate means of metal cutting.

Other features of the invention will become apparent by reference to the following description of the invention and to the accompanying drawings.

BRIEF DESCRIPTION OF THE DRAWINGS

FIG. 1A is a top plan view of a formed component comprising one half of the scissors in accordance with one embodiment of the invention.

FIG. 1B is a side view of the component shown in FIG. 1A.

DETAILED DESCRIPTION OF THE INVENTION

Figure 2:
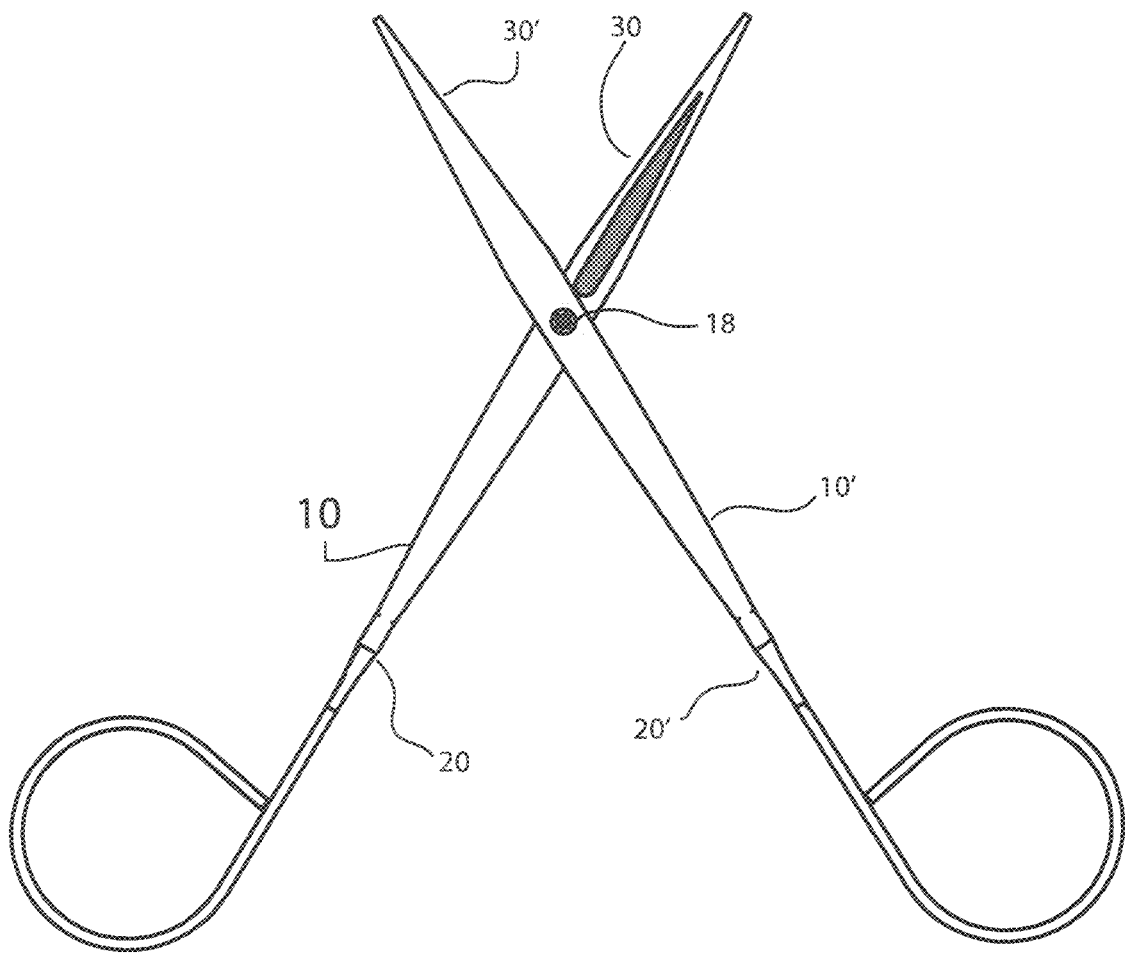
FIG. 2 is a top plan view of an embodiment of the inventive scissors as assembled with the handles and blades shown in an open position.

With reference to the Drawings and specifically FIG. 1A a sheet metal blank strip is shown fully formed into the component half of the inventive scissors 10. The scissors component has a handle end 12 and an operative or working end 14. An aperture 16 serves as the location for a pivot 18 joining component parts which forms the pair of inventive scissors 10, 10' as in the assembly shown in FIG. 2. The hole or aperture 16 for the pivot 18 is located at a point between the handle end 12 and the operative end 14. The actual pivot element 18 which keeps the scissors components in alignment can be a rivet, screw, pin or any other appropriate device for pivotally joining the two component parts 10, 10'.

Each component pair of scissors 10 or 10' is structurally complementary to the other component and are mechanically aligned and mated when assembled. Therefore, the 90 degree twist in the sheet metal components 10, 10' at a portion 20, 20' of each scissors between the handle ends and the operative ends enable the formation of an engagement point or hard stop when the pair of scissors are fully closed.

Figure 6:
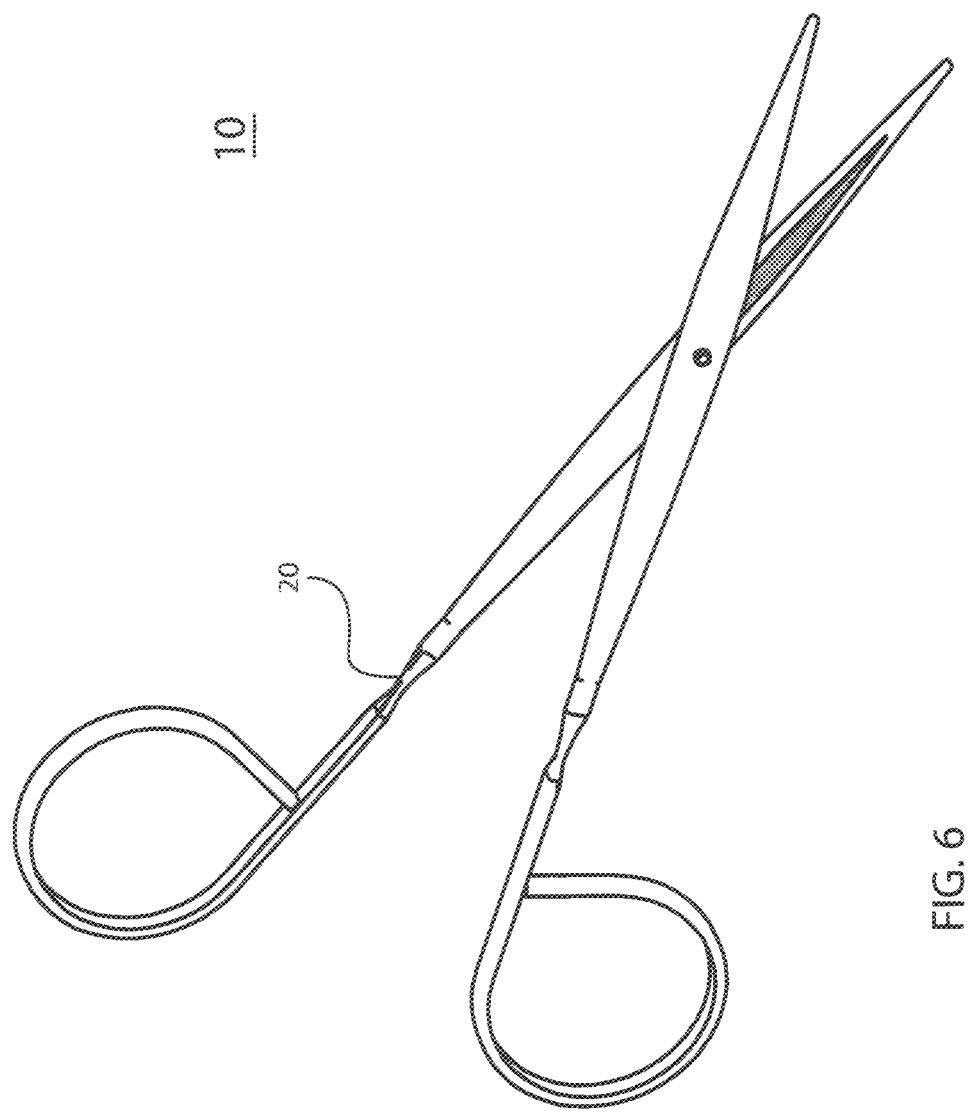
FIG. 6 is a perspective view of the embodiment of the scissors shown in FIG. 2.

FIG. 6 in particular is illustrative of the 90 degree twist regions in each component of the scissors.

Figure 3:
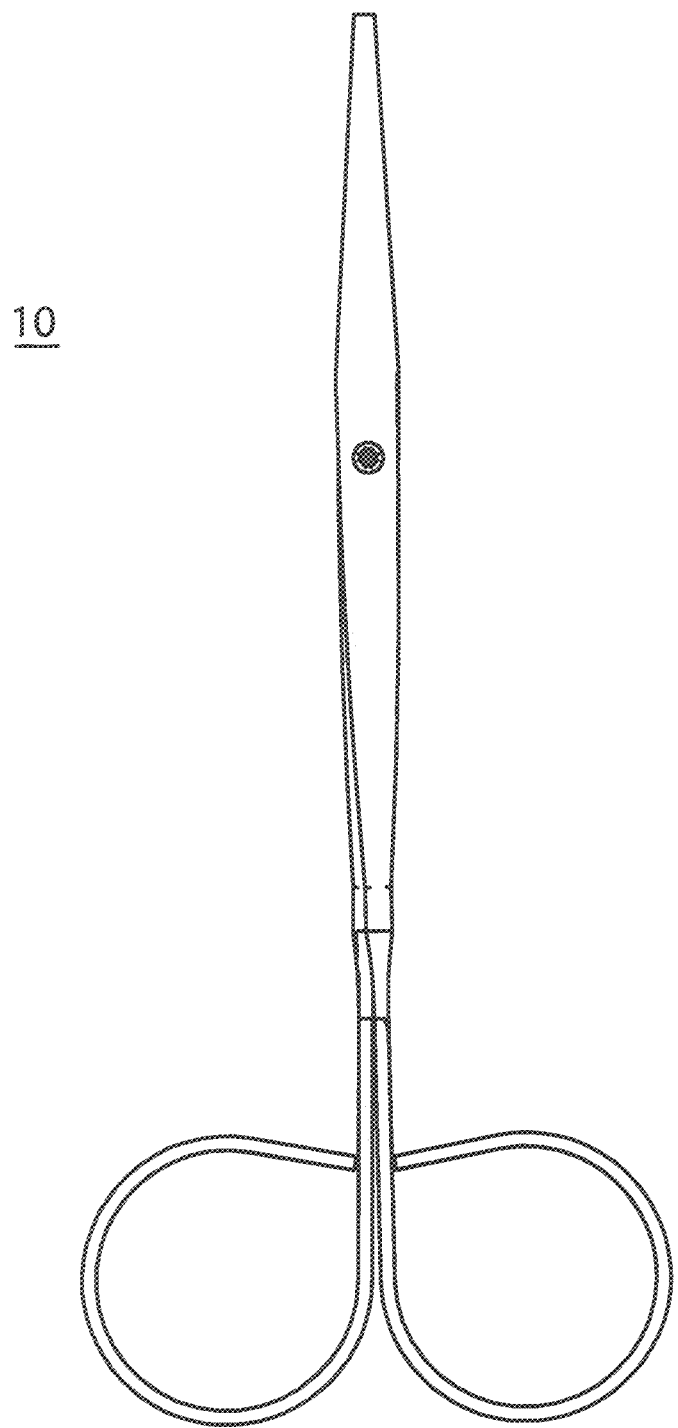
FIG. 3 is a top plan view of the scissors shown in FIG. 2 in a closed position.
Figure 4:
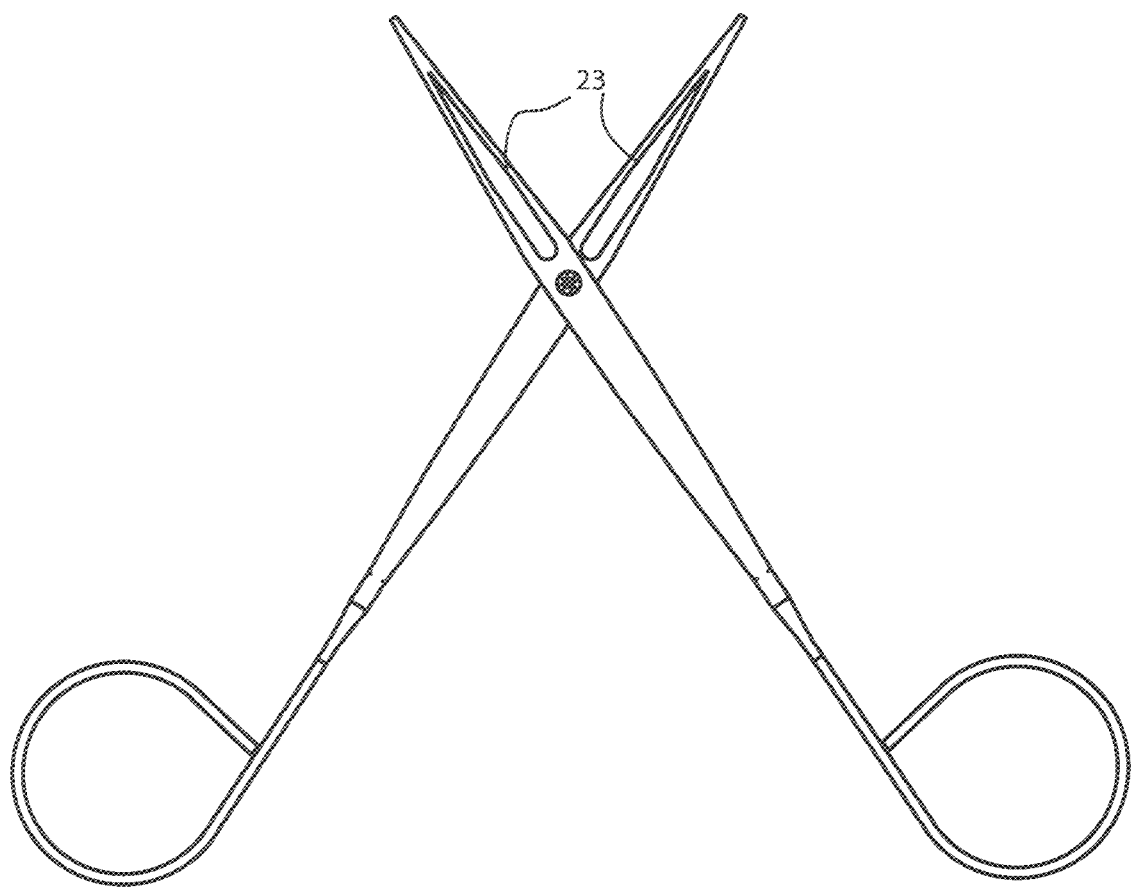
FIG. 4 is a top plan view of a second embodiment of the inventive scissors as assembled with the handles and blades shown in an open position.
Figure 5:
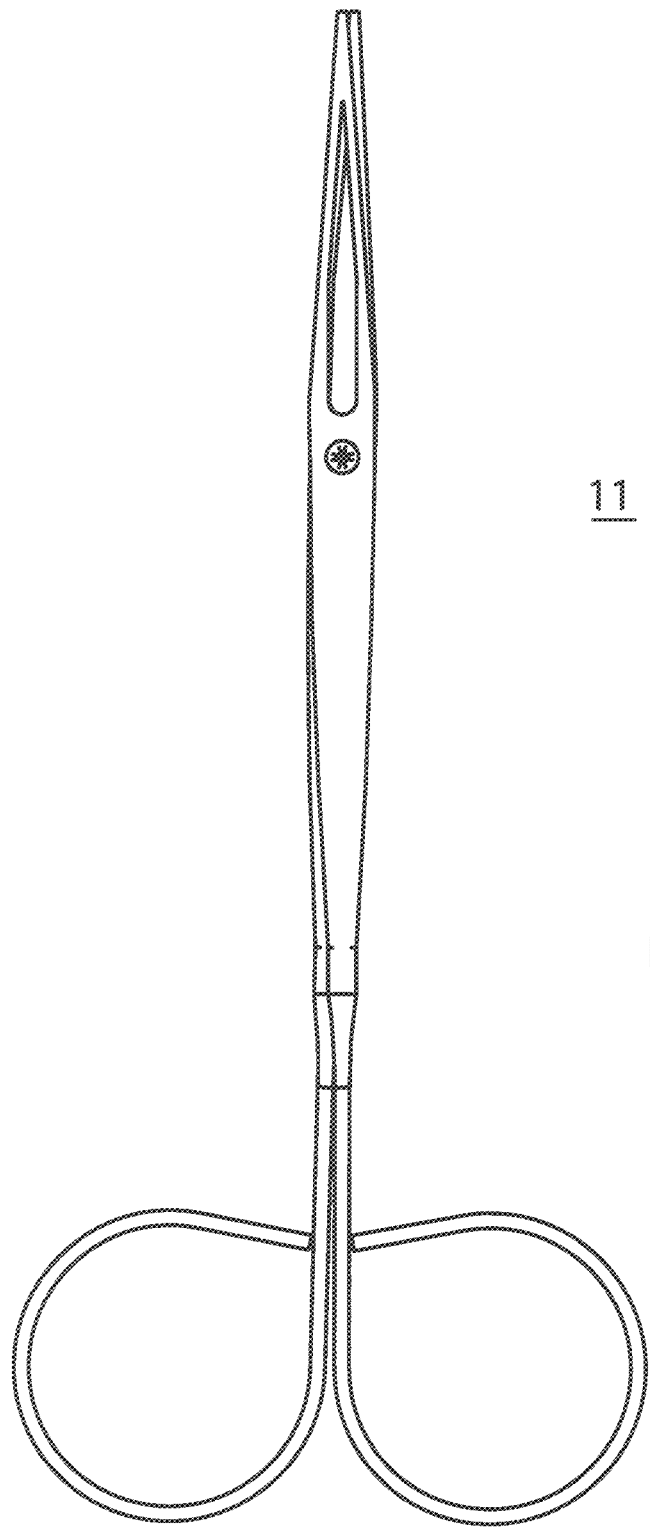
FIG. 5 is a top plan view of the scissors shown in FIG. 4 in a relatively closed position.
Figure 8:
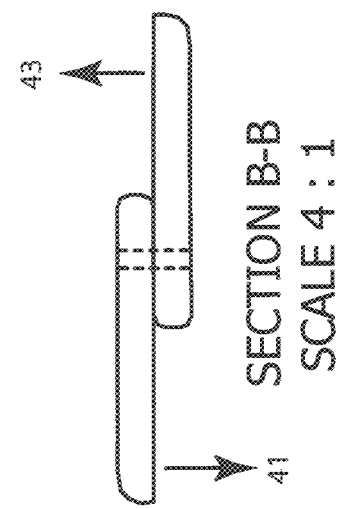
FIG. 8 is a side view of assembled embodiments of the inventive scissors together with a scaled view taken across section B-B of an end on view of the tips of the inventive scissors in an open position.

The cutting regions 30, 30' of each complementary component scissors 10, 10' are located adjacent the region 21 where a mass of material has been reduced as shown in FIG. 1A or removed entirely as shown at 23 in FIG. 4 in the example of the second embodiment depicted generally by underlined numeral 11. Mechanical biasing introduced during the fabricating process in this area of the working end 14 of the instrument induces a springy tendency for each component portion 14 to mutually bend against one another. This has the effect of insuring proper engagement of the scissor blade edges 30 when the scissors are closed—that is, when the handles are brought together (FIGS. 3 and 5). When the handles are separated and the blades open pulling away from one another, as in FIGS. 2,4,6 and 8, the tips or most forward portion of each scissors blade curves vertically, orthogonal to the pivotal plane of action of the scissors. This tendency imparted during manufacture to deflect vertically in a downward or upward curve is indicated by numerals 41—deflection downward, and 43—deflection upward, in the Section drawing B-B of the end view of the scissors shown in side elevation in FIG. 8.

Figure 7:
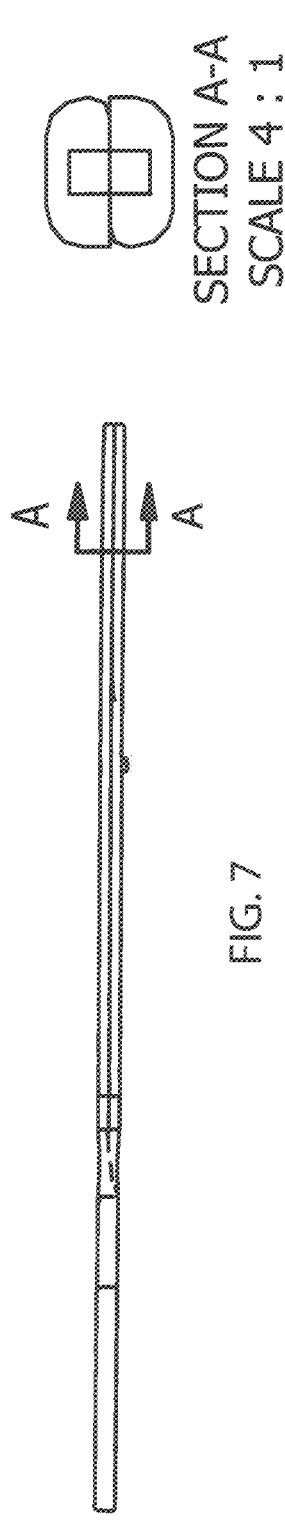
FIG. 7 is a side view of assembled embodiments of the inventive scissors together with a scaled view taken across section A-A of an end on view of the tips of the inventive scissors in a closed position.

When the scissors are closed as depicted in FIG. 3 and particularly in FIG. 7 and the drawing Section A-A, the pair of scissors components are maintained perfectly flat against one another.

The mutually biasing tendency of the operative ends of each scissor component insures proper shearing bias for cutting tissue and supplies augmented utility for purposes of blunt dissection. During conventional surgical operating procedures blunt dissection of tissue is necessary to reach a particular location within the body. The surgeon clinician often uses a surgical scissors to carefully separate and open spaces between layers of tissue using the bluntly pointed end of the scissors. The embodiments of the scissors described in the present in enables the surgeon to obtain a taller field of view when the scissors is opened due to the particularly flexible characteristic of the operative end of the instrument.

A portion of each scissors distal from the handle end 12, is used for blunt dissection. The arrow shaped point of the scissors is blunt and the edges are rounded to limit damage to tissue during dissection or examination of a particular area. Behind the bluntly pointed end of the instrument but more forward than the blade area 30 as shown in FIG. 1A, is a region 24, in the operative end 14 of the instrument which may be used for gripping or holding. In this construction, the inventive scissors has the capability to function as a blunt dissector, a scissors and a gripper.

In the preferred embodiments, the ring handled scissors instruments are formed from heat treatable, medical grade stainless steels though the device can be fabricated with other materials. In order to maintain the rigidity required for the ring handle portions and the integrally extended beam from the ring handle forward, the thickness of the stainless steel strip must be in excess of 1.53 mm (0.060"). However, in order to be flexible enough to create the additional shearing bias required for precision cutting, the thicknesses of the blade portions cannot exceed 0.89 mm (0.035"). As a consequence the inventive scissors utilizes the modification of the blade region described resulting in the edge region 30 of the blade of each scissors component needing at most 1 or 2 mm in width on its cutting edge. The remaining material after modifications described in region 21 in FIG. 1A should be no thicker than 1 mm (0.040") in order to increase flexibility and reduce drag upon closure of the scissors.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

We claim:

1. A ring handled pair of scissors constructed of medical grade, flexibly resilient, sheet metal strip material comprising:
 a first scissor component having a handle end and a working or operative end, said handle end of said first scissor component formed into a rigid ring shaped handle adapted to fit a clinician's finger;
 a beam portion extending from the ring shaped handle in excess of 1.53 mm (0.060") in thickness extending forward to said operative end;
 said operative end having a scissor blade portion of less than 0.89 mm (0.035") in thickness wherein a mass of material adjacent a cutting region of said scissor blade portion, shy of 1 or 2 mm from an edge of the scissor blade portion, is dished out in order to reduce the mass, a remaining mass of material adjacent the cutting region of said scissor blade portion to be no thicker than 1 mm (0.040") in order to increase flexibility and to reduce drag upon closure, permitting the scissor blade portion to flex orthogonally with respect to a plane of scissors action;
  an arrow shaped portion beyond the cutting region of the scissor blade portion distal from the handle end is blunt with rounded edges for purposes of blunt dissection;
 a second scissor component having a handle end and a working or operative end is structurally complementary to said first scissor component and is mechanically aligned and mated to said first scissor component by a pivot element for pivotally joining the first scissor component to the second scissor component enabling the flexible scissor blade portions of the first scissor component and the second scissor component to mutually bend against each other insuring proper engagement of the edges of the scissor blade portions as the scissors are closed;
 a 90 degree twist in each of the scissor components enable the formation of a hard stop when the pair of scissors are fully closed.

2. A ring handled pair of scissors constructed of medical grade, flexibly resilient, sheet metal strip material comprising:
 a first scissor component having a handle end and a working or operative end, said handle end of said first scissor component formed into a rigid ring shaped handle adapted to fit a clinician's finger;
 a beam portion extending from the ring shaped handle in excess of 1.53 mm (0.060") in thickness extending forward to said operative end;
 said operative end having a scissor blade portion of less than 0.89 mm (0.035") in thickness wherein a mass of material adjacent a cutting region of said scissor blade portion, shy of 1 or 2 mm from an edge of the scissor blade portion, is removed entirely in order to reduce the mass, a remaining mass of material adjacent the cutting region of said scissor blade portion to be no thicker than 1 mm (0.040") in order to increase flexibility and to reduce drag upon closure, permitting the scissor blade portion to flex orthogonally with respect to a plane of scissors action;

an arrow shaped portion beyond the cutting region of the scissor blade portion distal from the handle end is blunt with rounded edges for purposes of blunt dissection;

a second scissor component having a handle end and a working or operative end is structurally complementary to said first scissor component and is mechanically aligned and mated to said first scissor component by a pivot element for pivotally joining the first scissor component to the second scissor component enabling the flexible scissor blade portions of the first scissor component and the second scissor component to mutually bend against each other insuring proper engagement of the edges of the scissor blade portions as the scissors are closed;

a 90 degree twist in each of the scissor components enable the formation of a hard stop when the pair of scissors are fully closed.

\* \* \* \* \*